US00PP28764P3

(12) United States Plant Patent
Hammett

(10) Patent No.: US PP28,764 P3
(45) Date of Patent: Dec. 12, 2017

(54) *DAHLIA* PLANT NAMED '71853-09'

(50) Latin Name: *Dahlia hybrida*
Varietal Denomination: 71853-09

(71) Applicant: Keith Hammett, Auckland (NZ)

(72) Inventor: Keith Hammett, Auckland (NZ)

( * ) Notice: Subject to any disclaimer, the term of this patent is extended or adjusted under 35 U.S.C. 154(b) by 126 days.

(21) Appl. No.: 14/757,045

(22) Filed: Nov. 12, 2015

(65) Prior Publication Data

US 2016/0183437 P1 Jun. 23, 2016

(30) Foreign Application Priority Data

Dec. 10, 2014 (NZ) ..... 32441

(51) Int. Cl.
*A01H 5/02* (2006.01)

(52) U.S. Cl.
USPC ..... Plt./321

(58) Field of Classification Search
USPC ..... Plt./263.1, 321
See application file for complete search history.

*Primary Examiner* — Susan McCormick Ewoldt
*Assistant Examiner* — Karen Redden

(57) ABSTRACT

A new cultivar of *Dahlia* plant named '71853-09' that is characterized by an upright and uniform growth habit, red-brown compound leaves, a cactus type inflorescence and red-purple ray florets.

1 Drawing Sheet

Botanical classification: *Dahlia hybrida.*
Variety denomination: '71853-09'.

BACKGROUND OF THE INVENTION

The present invention relates to a new and distinct cultivar of *Dahlia* plant botanically known as *Dahlia hybrida* and hereinafter referred to by the cultivar name '71853-09'.

The new cultivar is the product of a breeding program conducted by the inventor in a cultivated area of Auckland, New Zealand. The objective of the breeding program is to develop new *Dahlia* cultivars with interesting and unique flower colors.

'71853-09' originated from the crossing of the female or seed parent *Dahlia* 'Kindred Spirit' (not patented) and the male or pollen parent an unidentified *Dahlia* cultivar (not patented). The cultivar '71853-09' was selected by the inventor in 2012 as a single plant within the progeny of the stated cross in a controlled environment of Auckland, New Zealand.

Asexual reproduction by terminal cuttings of the new cultivar '71853-09' was first performed in 2012 in Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Dahlia* cultivar '71853-09'. These traits in combination distinguish '71853-09' as a new and distinct cultivar apart from all other existing varieties of *Dahlia* known to the inventor.

1. *Dahlia* '71853-09' exhibits an upright and uniform growth habit.
2. *Dahlia* '71853-09' exhibits red-brown compound leaves.

3. *Dahlia* '71853-09' exhibits a cactus type inflorescence.
4. *Dahlia* '71853-09' exhibits red-purple ray florets.

The closest comparison varieties are *Dahlia* 'Tomorrow' (not patented) and *Dahlia* 'Spin City' (not patented). '71853-09' is different than 'Tomorrow' in having red-purple flowers. The flowers of 'Tomorrow' are pink. '71853-09' is different than 'Spin City' in having red-purple flowers. The flowers of 'Spin City' are pink.

The new cultivar '71853-09' is distinguishable from the female or seed parent plant 'Kindred Spirit' in having red-purple flowers. In contrast, the flowers of 'Kindred Spirit' are yellow.

The new cultivar '71853-09' is distinguishable from the unidentified male or pollen parent plant in having red-purple flowers. In contrast, the flowers of the unidentified male or pollen parent plant are red.

BRIEF DESCRIPTION OF THE DRAWING

The accompanying photograph illustrates the distinguishing traits of *Dahlia* '71853-09'. The plant in the photograph shows an overall view of 20 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Dahlia* cultivar named '71853-09'. Data was collected in Auckland, New Zealand from 20 week old outdoor grown plants in 12 cm. diameter containers. The time of year was June and the temperature averaged 17° Centigrade during the day and 10° Centigrade at night. The light level was natural outdoor light. Color determinations are in accordance with The Royal Horticultural Society Colour Chart 2001 edition, except where general color terms of ordinary dictionary significance are used. The growing requirements are similar to the species.

'71853-09' has not been tested under all possible conditions and phenotypic differences may be observed with variations in environmental, climatic, and cultural conditions, however, without any variance in genotype.

Botanical classification: *Dahlia* '71853-09'.

Use: Ornamental.

Parentage: '71853-09' is a hybrid plant that resulted from the induced hybridization of the following parent plants:

*Female parent.*—*Dahlia* 'Kindred Spirit'.

*Male parent.*—An unidentified *Dahlia* cultivar.

Vigor: Moderate.

Growth habit: Broad upright.

Plant shape: Inverted triangle with flowers on top.

Suitable container size: 12 cm. container.

Height: 62 cm. in height.

Width: 26 cm. in width.

Hardiness: USDA Zone 8.

Propagation: Terminal cuttings.

Time to initiate roots: Approximately 12 days to produce roots on an initial cutting.

Time to produce a rooted cutting or liner: Approximately 28 days.

Crop time: From a rooted cutting, approximately 18 to 20 weeks are required to produce a finished flowering plant.

Root system: Fine and fibrous.

Root color: 158B.

Stem:

*Branching habit.*—Free branching.

*Average number of lateral branches.*—8.

*Pinching.*—Yes.

*Lateral branch diameter.*—7 mm. in diameter.

*Lateral branch length.*—46 cm. in length.

*Lateral branch strength.*—High.

*Stem color.*—197A.

*Pubescence.*—Absent.

*Internode length.*—2.2 cm. between nodes.

*Shape.*—Round.

*Surface.*—Smooth, slightly glossy.

Foliage:

*Texture.*—Slightly glossy.

*Leaf arrangement.*—Opposite.

*Compound or single.*—Compound.

*Quantity of leaves per lateral branch.*—6.

*Quantity of leaflets per leaf.*—3.

*Leaf length.*—15.6 cm. in length.

*Leaf width.*—12.8 cm. in width.

*Leaflet length.*—5.1 cm. in length.

*Leaflet width.*—3.2 cm. in width.

*Leaf shape.*—Ovate.

*Leaf apex.*—Apiculate.

*Leaf base.*—Attenuate.

*Pubescence.*—Absent.

*Leaf margin.*—Serrate.

*Vein pattern.*—Pinnate.

*Young leaf color* (*lower surface*).—N186C.

*Young leaf color* (*upper surface*).—N186C.

*Mature leaf color* (*lower surface*).—N186C.

*Mature leaf color* (*upper surface*).—N186C.

*Vein color* (*lower surface*).—N186C.

*Vein color* (*upper surface*).—N186C.

*Leaf attachment.*—Petiolate.

*Petiole dimensions.*—9 mm. in length and 3 mm. in width.

*Petiole color.*—N189A.

Inflorescence:

*Inflorescence type.*—Cactus type inflorescence, borne on terminals arising from leaf axils, ray and disc florets develop acropetally on the receptacle.

*Inflorescence aspect.*—Upward and outward.

*Quantity of flowers per lateral stem.*—1 to 2.

*Quantity of flowers and buds per plant.*—Approximately 14.

*Flowering season.*—Summer and fall.

*Fragrance.*—Slight.

*Flower bud length.*—1.2 cm. in length.

*Flower bud diameter.*—1.4 cm. in diameter.

*Flower bud shape.*—Spherical.

*Bud color.*—189A, tip N74C.

*Flower aspect.*—Outward-upright.

*Flower dimensions.*—11.7 cm. in diameter and 8.6 cm. in height.

*Flower longevity.*—Approximately 12 days.

*Ray floret number.*—Approximately 125 per flower.

*Ray floret texture.*—Smooth.

*Ray floret fused or unfused.*—Unfused.

*Ray floret shape.*—Elongated oblong.

*Ray floret margin.*—Entire.

*Ray floret apex.*—Acute.

*Ray floret base.*—Attenuate.

*Ray floret venation pattern.*—Parallel.

*Ray floret dimensions.*—5.2 cm. in length and 8 mm. in width.

*Ray floret color when opening* (*upper side*).—N74B.

*Ray floret color when opening* (*under side*).—N74B.

*Ray floret color fully open* (*upper side*).—N74A.

*Ray floret color fully open* (*under side*).—N74A.

*Disc floret number.*—Approximately 40 per flower.

*Disc floret texture.*—Smooth.

*Disc floret shape.*—Tubular.

*Disc floret apex.*—Acute.

*Disc floret dimensions.*—8 mm. in length and 3 mm. in width.

*Disc floret color* (*upper side*).—13C.

*Disc floret color* (*under side*).—13C.

*Receptacle dimensions.*—5 mm. in depth and 2.3 cm. in diameter.

*Receptacle surface.*—Smooth.

*Receptacle color.*—13C.

*Self-cleaning or persistent.*—Self-cleaning.

Peduncle:

*Peduncle dimensions.*—23 cm. in length and 4 mm. in diameter.

*Peduncle angle.*—0°.

*Peduncle color.*—197A.

*Peduncle strength.*—Strong.

Phyllaries:

*Arrangement.*—Reflexed, involucral bracts.

*Quantity.*—6.

*Length.*—10 to 11 mm.

*Width.*—4 to 5 mm.

Reproduction organs:

*Stamen number.*—5 in number on disc florets only.

*Anther dimensions.*—5 mm. in length.

*Anther color.*—12B.

*Amount of pollen.*—Low.

*Pollen color.*—12B.

*Pistil number.*—One, on both ray and disc florets.
*Pistil length.*—6 mm.
*Stigma dimensions.*—1 mm. in length and 0.4 mm. in width.
*Stigma color.*—12A.
*Ovary color.*—5B.

Fruit and seed: Fruit and seed production has not been observed to date.

Disease resistance: Plants of the new *dahlia* have not been observed for disease resistance.

The invention claimed is:

1. A new and distinct variety of *Dahlia* plant named '71853-09' as described and illustrated.

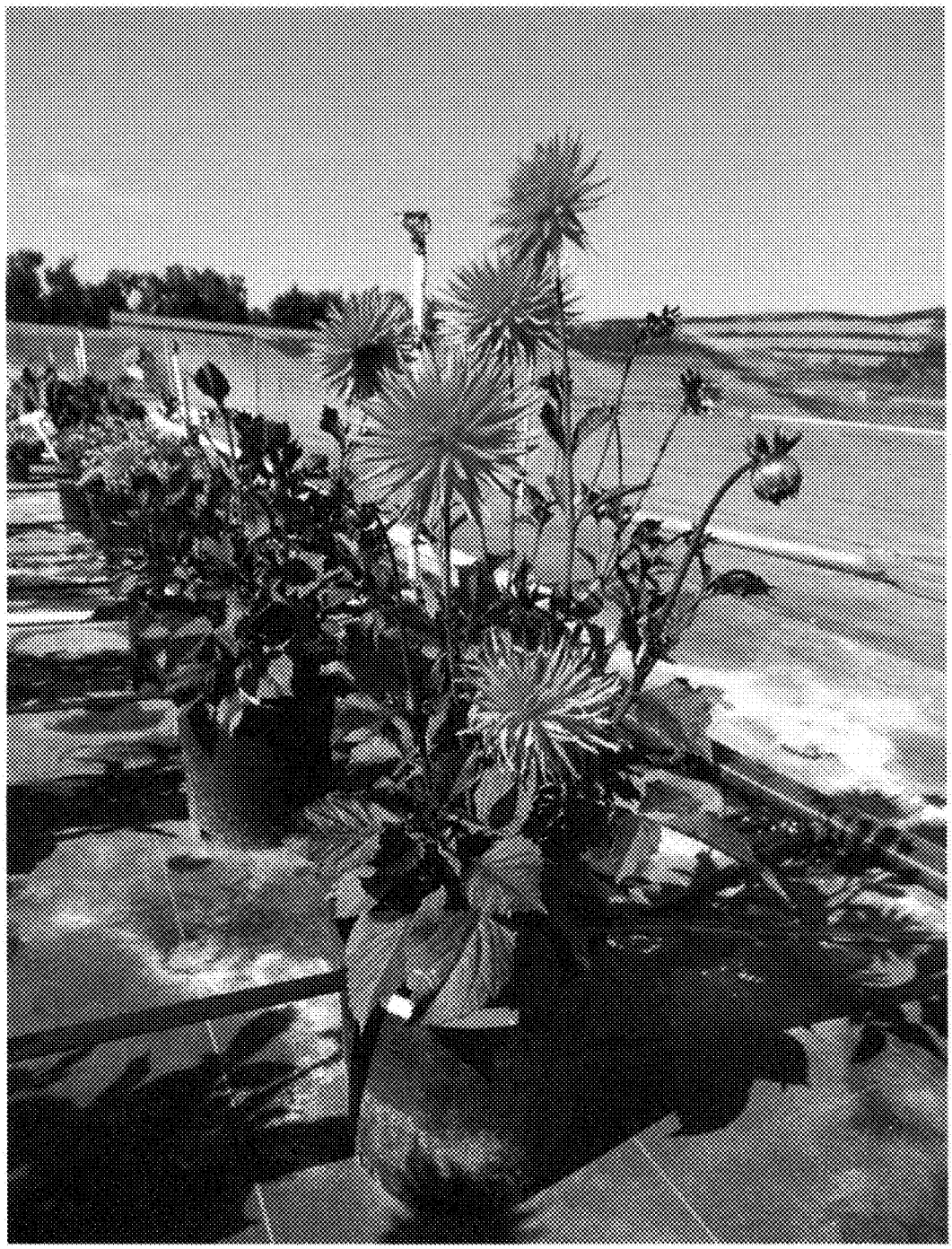

* * * * *